US012694963B2

(12) United States Patent
Nguyen et al.

(10) Patent No.: US 12,694,963 B2
(45) Date of Patent: Jul. 28, 2026

(54) METHODS AND SYSTEMS OF EMBODIMENT TRAINING IN A VIRTUAL-REALITY ENVIRONMENT

(71) Applicants: Lincoln Nguyen, san francisco, CA (US); Lewey Alec Geselowitz, san francisco, CA (US); Michael Scott Trujillo, Benicia, CA (US)

(72) Inventors: Lincoln Nguyen, san francisco, CA (US); Lewey Alec Geselowitz, san francisco, CA (US); Michael Scott Trujillo, Benicia, CA (US)

( * ) Notice: Subject to any disclaimer, the term of this patent is extended or adjusted under 35 U.S.C. 154(b) by 0 days.

(21) Appl. No.: 16/380,425

(22) Filed: Apr. 10, 2019

(65) Prior Publication Data

US 2020/0168311 A1 May 28, 2020

Related U.S. Application Data

(63) Continuation-in-part of application No. 16/202,068, filed on Nov. 27, 2018, now abandoned.

(Continued)

(51) Int. Cl.
*G16H 20/30* (2018.01)
*G06F 3/01* (2006.01)
(Continued)

(52) U.S. Cl.
CPC ............. *G16H 20/30* (2018.01); *G06F 3/011* (2013.01); *G06T 19/003* (2013.01); *G16H 20/70* (2018.01)

(58) Field of Classification Search
CPC ........ G16H 50/30; G16H 20/30; G16H 20/70; G06F 3/011; G06T 19/003
See application file for complete search history.

(56) References Cited

U.S. PATENT DOCUMENTS 9,892,655 B2 * 2/2018 Snow .................... G16H 40/67
2011/0230792 A1 * 9/2011 Sarig-Bahat ......... A61B 5/1124
600/595

(Continued)

FOREIGN PATENT DOCUMENTS

WO WO-2007121570 A1 * 11/2007 ......... G06F 19/3418

OTHER PUBLICATIONS

C. Camporesi, M. Kallmann and J. J. Han, "VR solutions for improving physical therapy," 2013 IEEE Virtual Reality (VR), 2013, pp. 77-78, doi: 10.1109/VR.2013.6549371. (Year: 2013).*

*Primary Examiner* — Sheetal R Paulson

(57) ABSTRACT

A computerized method for correlating features of a user's motion in a VR-based exercise with specified populations includes the step of tracking a user's motion in a VR-based exercise with a hand controller. Based on a set of datapoints obtained from a sequence of positions of the hand controller, the method extracts a dynamic range of the user's motion. Based on the dynamic range, the method determines a velocity, an acceleration of the user's motion. The method determines the coefficient of variation for the velocity and the acceleration. From the acceleration and velocity data, the method calculates an initiation of the user's motion. The method calculates a combinatorial statistic from the coefficient of variation for the velocity ad the acceleration. The method determines a set of features of the user's motion represented by the combinatorial statistic that correlates to another combinatorial statistic associated with a specified population.

4 Claims, 15 Drawing Sheets

Related U.S. Application Data

(60) Provisional application No. 62/821,449, filed on Mar. 21, 2019.

(51) Int. Cl.
  _G06T 19/00_    (2011.01)
  _G16H 20/70_    (2018.01)

(56)                  References Cited

U.S. PATENT DOCUMENTS

| | | | |
|---|---|---|---|
| 2016/0086500 A1* | 3/2016 | Kaleal, III ............. | G06Q 10/10 |
| | | | 434/257 |
| 2019/0065970 A1* | 2/2019 | Bonutti .................. | G06N 5/045 |
| 2020/0185097 A1* | 6/2020 | Orr ......................... | G16H 20/30 |
| 2021/0401365 A1* | 12/2021 | Höynälä ................ | G16H 40/63 |

* cited by examiner

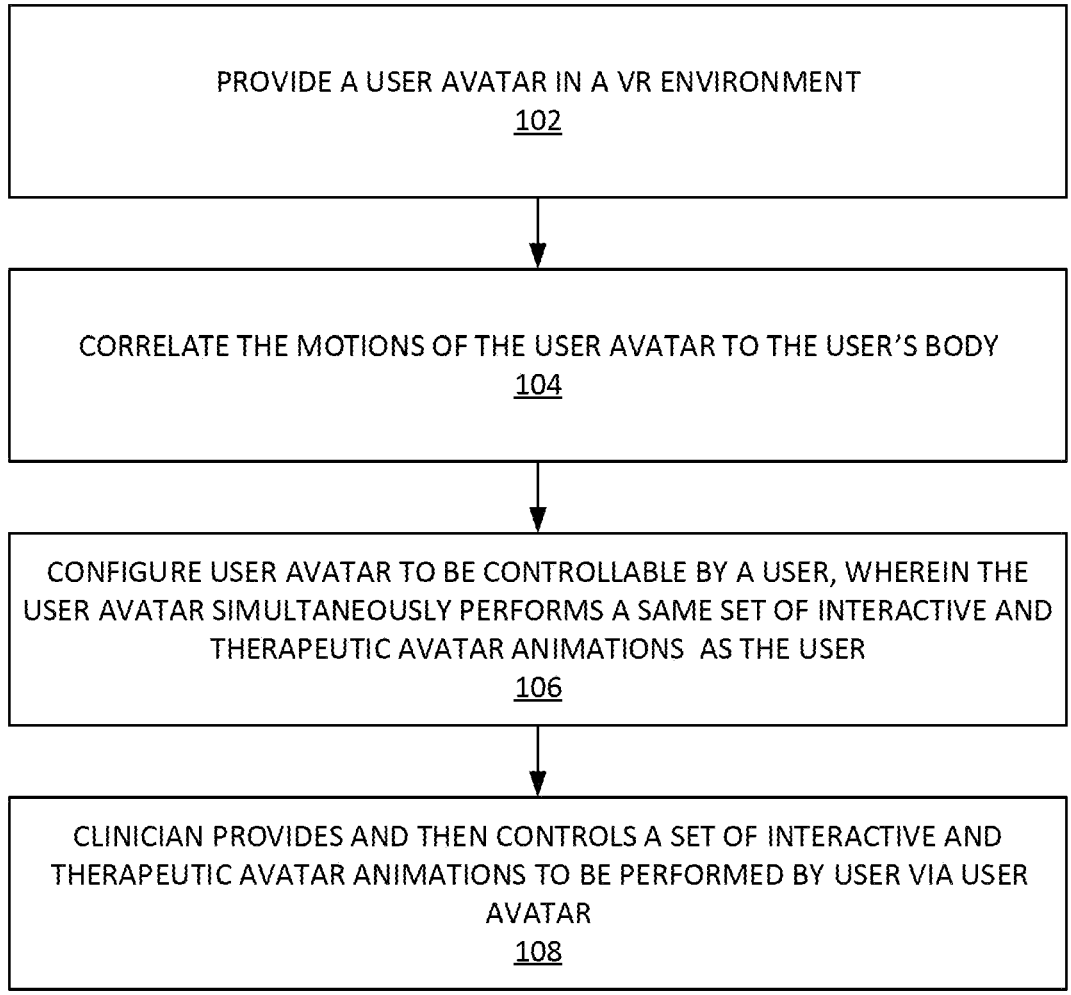

PROVIDE A USER AVATAR IN A VR ENVIRONMENT
102

CORRELATE THE MOTIONS OF THE USER AVATAR TO THE USER'S BODY
104

CONFIGURE USER AVATAR TO BE CONTROLLABLE BY A USER, WHEREIN THE USER AVATAR SIMULTANEOUSLY PERFORMS A SAME SET OF INTERACTIVE AND THERAPEUTIC AVATAR ANIMATIONS AS THE USER
106

CLINICIAN PROVIDES AND THEN CONTROLS A SET OF INTERACTIVE AND THERAPEUTIC AVATAR ANIMATIONS TO BE PERFORMED BY USER VIA USER AVATAR
108

IDENTIFY A BODY PART RELATED TO THE THERAPEUTIC NEED OF THE USER
202

GENERATE VR ELEMENT REPRESENTING THE BODY PART
204

INCORPORATE A VR ELEMENT INTO THE USER AVATAR
206

MANIPULATE THE ANGLE OF MOVEMENT AND/OR THE GAIN OF THE VR ELEMENT WITH RESPECT TO ACTUAL PHYSICAL MOVEMENT OF THE BODY PART
208

ENABLE CLINICIAN TO SET THE ANGLE OF MOVEMENT AND/OR THE GAIN IN REALTIME
210

200

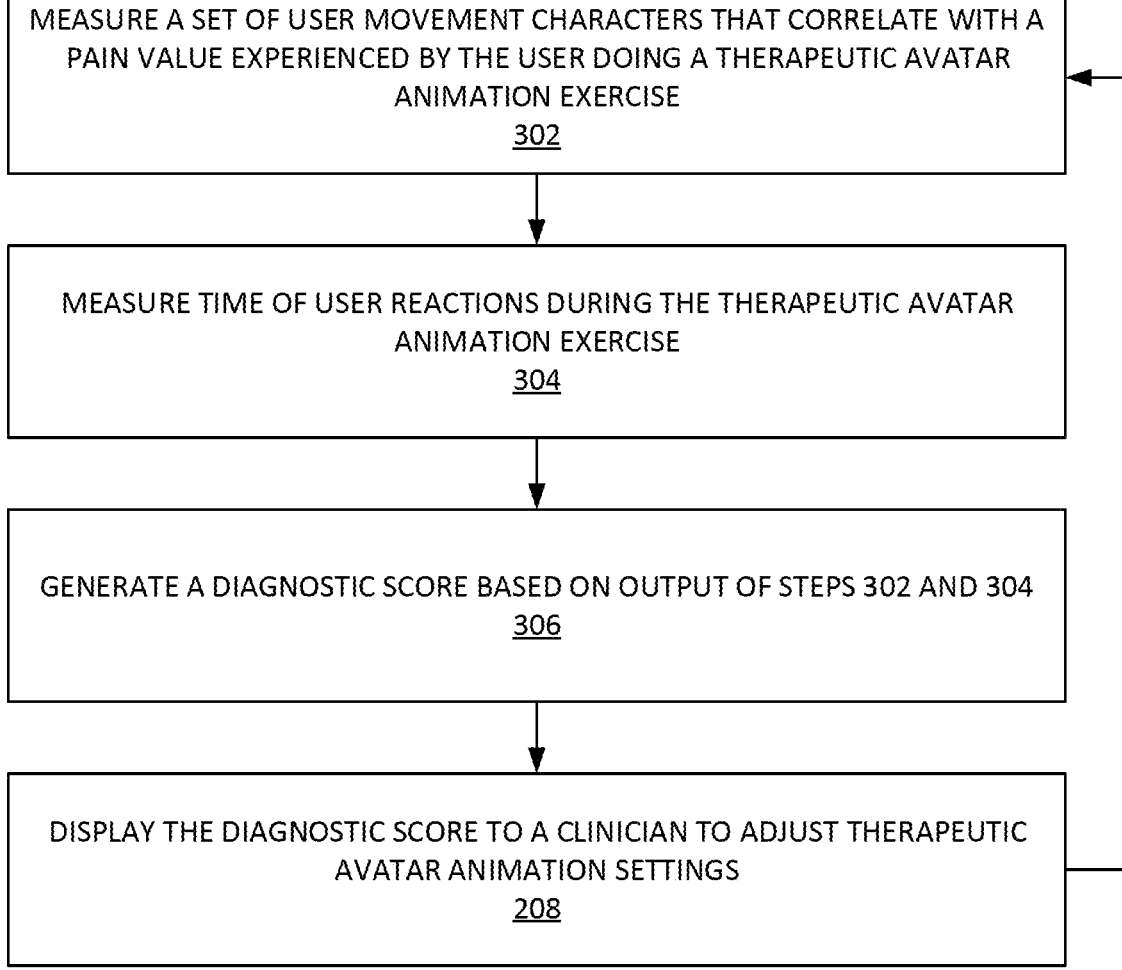

MEASURE A SET OF USER MOVEMENT CHARACTERS THAT CORRELATE WITH A PAIN VALUE EXPERIENCED BY THE USER DOING A THERAPEUTIC AVATAR ANIMATION EXERCISE
302

MEASURE TIME OF USER REACTIONS DURING THE THERAPEUTIC AVATAR ANIMATION EXERCISE
304

GENERATE A DIAGNOSTIC SCORE BASED ON OUTPUT OF STEPS 302 AND 304
306

DISPLAY THE DIAGNOSTIC SCORE TO A CLINICIAN TO ADJUST THERAPEUTIC AVATAR ANIMATION SETTINGS
208

CREATE A CONDITION SURROUNDING THE THERAPEUTIC AVATAR ANIMATION
EXERCISE MOVEMENT THAT IS PAIN FREE
402

DETERMINE THAT SENSORY CONDITIONS OF STEP 402 HAVE BECOME
ASSOCIATED WITH SAFETY
404

FOR A MORE CHALLENGING THE THERAPEUTIC AVATAR ANIMATION EXERCISE
PROVIDE SENSORY CONDITIONS OF STEP 402 PRIOR TO THE EXERCISE
406

400

—700

OBTAIN USER INFORMATION RELEVANT TO THERAPEUTIC
EXERCISE
902

FACTOR OUTPUT OF STEP 902 AGAINST NATIONAL MODEL(S)
FOR WHAT ROM SHOULD BE
904

PROVIDE A VR VIEW OF AN AVATAR PERFORMING THERAPEUTIC
EXERCISE BASED ON OUTPUT OF 904
906

USER PERFORMS THERAPEUTIC EXERCISES AND TRACK USER
PERFORMANCE THEREOF
908

GENERATE A VR VIEW OF AN AVATAR PERFORMING OF THE
USER PERFORMING THERAPEUTIC EXERCISE BASED ON OUTPUT
OF 908
910

ADJUST VR VIEW OF USER'S AVATAR AT SPECIFIED PORTIONS OF
THE THERAPEUTIC EXERCISE TO SIMULATE AND/OR
APPROXIMATE NATIONAL MODELS
912

900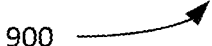

FIGURE 9

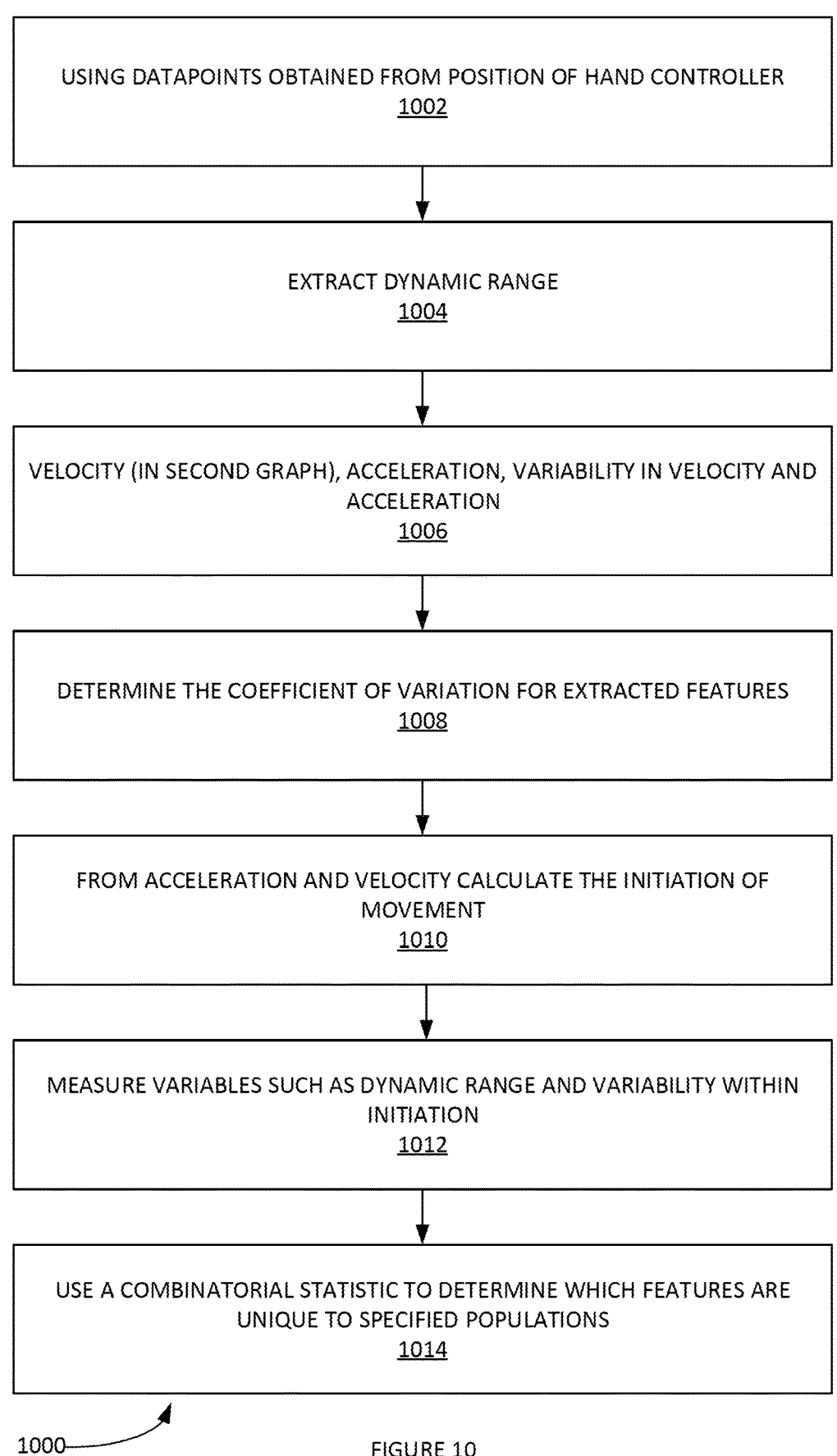

USING DATAPOINTS OBTAINED FROM POSITION OF HAND CONTROLLER
1002

EXTRACT DYNAMIC RANGE
1004

VELOCITY (IN SECOND GRAPH), ACCELERATION, VARIABILITY IN VELOCITY AND ACCELERATION
1006

DETERMINE THE COEFFICIENT OF VARIATION FOR EXTRACTED FEATURES
1008

FROM ACCELERATION AND VELOCITY CALCULATE THE INITIATION OF MOVEMENT
1010

MEASURE VARIABLES SUCH AS DYNAMIC RANGE AND VARIABILITY WITHIN INITIATION
1012

USE A COMBINATORIAL STATISTIC TO DETERMINE WHICH FEATURES ARE UNIQUE TO SPECIFIED POPULATIONS
1014

Extract features:

Normal
X Dynamic Range: 0.12
Y Dynamic Range: 1.355
Z Dynamic Range: 0.4830

Guarded
X Dynamic Range: 0.145
Y Dynamic Range: 1.1380
Z Dynamic Range: 0.4980

Normal Coefficient of
Variation
X: 0.1336
Y: -0.8239
Z: 0.8438

Guarded Coefficient
of Variation
X: 0.2346
Y: -0.8223
Z: 0.7552

1202

1204

1206

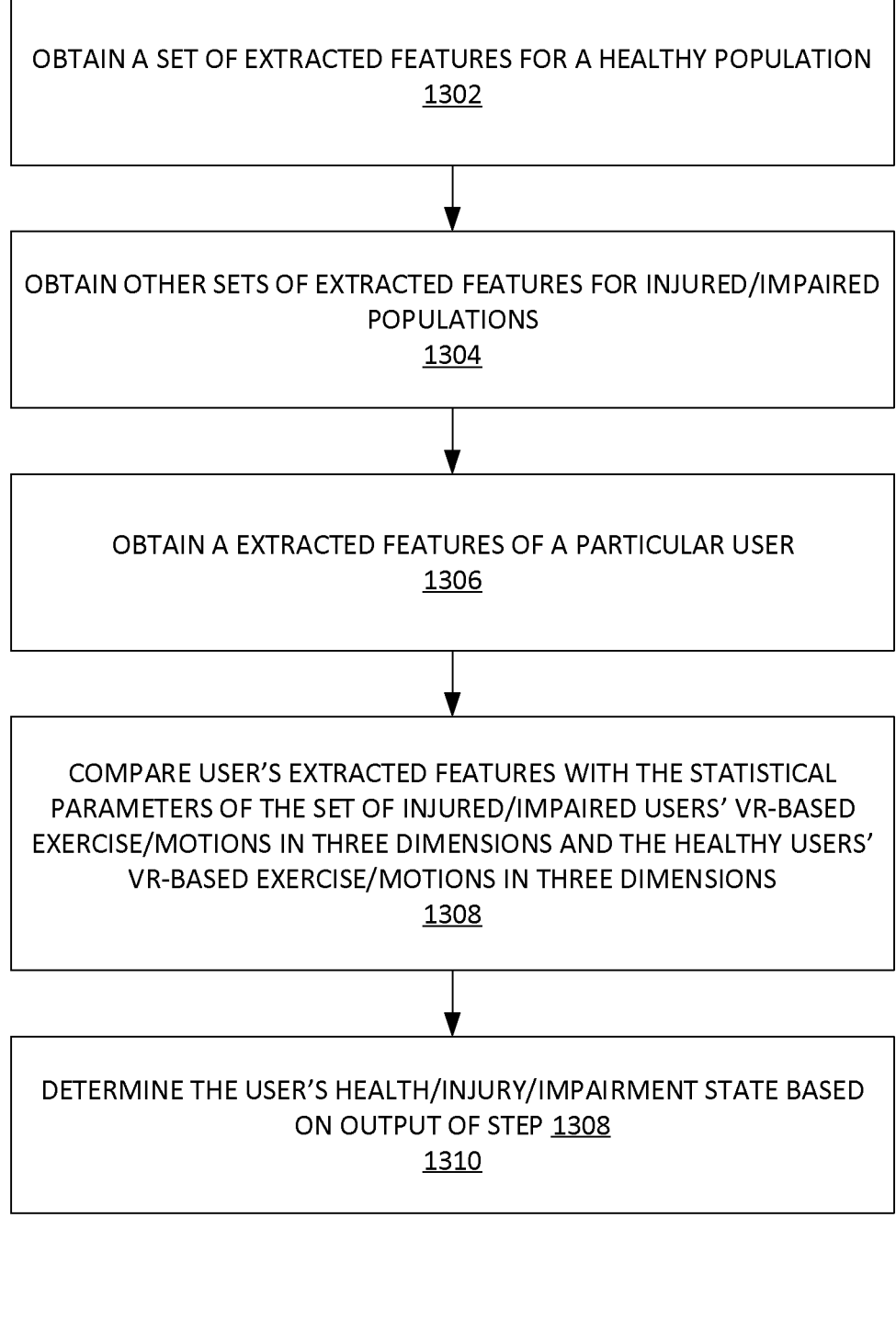

OBTAIN A SET OF EXTRACTED FEATURES FOR A HEALTHY POPULATION
1302

OBTAIN OTHER SETS OF EXTRACTED FEATURES FOR INJURED/IMPAIRED POPULATIONS
1304

OBTAIN A EXTRACTED FEATURES OF A PARTICULAR USER
1306

COMPARE USER'S EXTRACTED FEATURES WITH THE STATISTICAL PARAMETERS OF THE SET OF INJURED/IMPAIRED USERS' VR-BASED EXERCISE/MOTIONS IN THREE DIMENSIONS AND THE HEALTHY USERS' VR-BASED EXERCISE/MOTIONS IN THREE DIMENSIONS
1308

DETERMINE THE USER'S HEALTH/INJURY/IMPAIRMENT STATE BASED ON OUTPUT OF STEP 1308
1310

METHODS AND SYSTEMS OF EMBODIMENT TRAINING IN A VIRTUAL-REALITY ENVIRONMENT

CLAIM OF PRIORITY AND INCORPORATION BY REFERENCE

This application claims priority from U.S. Application No. 62/821,449, filed on 21 Mar. 2019. This application is hereby incorporated by reference in its entirety for all purposes.

This application claims priority from U.S. application Ser. No. 16/202,068, filed on 27 Nov. 2018. U.S. application Ser. No. 16/202,068 claims priority from U.S. Provisional Application No. 62/590,925, filed 27 Nov. 2017. These applications are hereby incorporated by reference in their entirety for all purposes.

FIELD OF THE INVENTION

The invention is in the field of virtual reality and more specifically to a method, system and apparatus for embodiment training in a virtual-reality environment.

DESCRIPTION OF THE RELATED ART

Virtual reality can provide an immersive experience for users. This immersive experience can be used to engage the user in various exercises and therapeutic movements. VR also offers a cost-effective tool to study and replicate interactions in a controlled environment. VR can be used in physical rehabilitation. This can be performed both in a therapist's office or at home. VR can provide therapeutic games and movements. VR can track user motions during these activities and provide the user with real-time feedback. In this way, VR can offer rehabilitation methods without sophisticated and expensive equipment. Accordingly, improvements to various VR rehabilitation methods are desired.

SUMMARY OF THE INVENTION

In one aspect, a computerized method for augmenting (virtual reality) VR-based therapeutic movements includes the step of obtaining a user range of motion (ROM) relevant to a VR-based therapeutic exercise. The method compares the user ROM against an aspirational model ROM for the VR-based therapeutic exercise. The method displays a VR view of an avatar of the user performing the VR-based therapeutic exercise. The method tracks a performance of the user of the VR-based therapeutic exercise. The method generates a VR view of the avatar performing of the user performing the VR-therapeutic exercise. The method adjusts the VR view of avatar at one or specified portions of the VR-therapeutic exercise to simulate the aspirational model ROM.

In another aspect, a computerized method for extracting and interpreting features of a user's motion in a VR-based exercise with specified populations includes the step of tracking a user's motion in a VR-based exercise with head mounted display two hand controllers. Based on a set of datapoints obtained from a sequence of positions of two hand controllers the method extracts motion characteristics of the user's motion. Based on motion characteristics, the method determines velocity, acceleration, dynamic range, and variability of the user's motion. The method determines the coefficient of variation for the velocity and the acceleration. From the acceleration and velocity data, the method calculates multivariate characteristic of motion. The method further classifies motion based on a combinatorial statistic from extracted features. The method determines a set of features of the user's motion represented by the combinatorial statistic that correlates to another combinatorial statistic associated with a specified population.

BRIEF DESCRIPTION OF THE DRAWINGS

FIG. 1 illustrates an example process for managing various therapeutic avatar animation exercises, according to some embodiments.

FIG. 3 illustrates an example process for generating a diagnostic score for a user performing therapeutic avatar animation exercises, according to some embodiments.

FIG. 9 illustrates an example process for augmenting VR-based therapeutic movements, according to some embodiments.

FIG. 10 illustrates an example process for correlating features of a user's motion in a VR-based exercise/motion with specified populations, according to some embodiments.

FIG. 13 illustrates an example process for utilizing extracted features obtained on the three dimensions of VR-based exercise/motion for an example user motion for diagnosis of health/injury/impairment, according to some embodiments.

Figure 2:
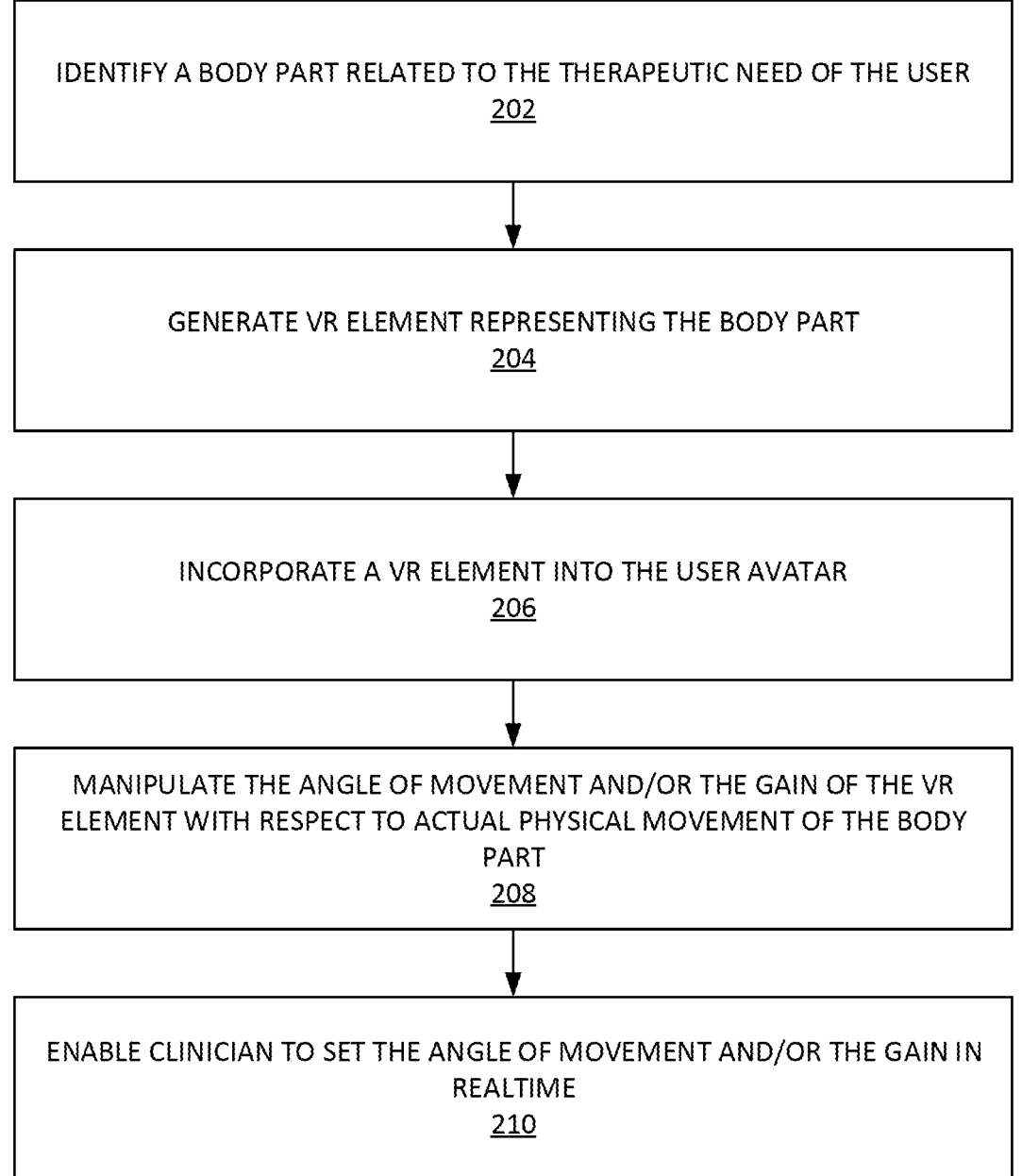
FIG. 2 illustrates an example process of therapeutic avatar animation exercise manipulation, according to some embodiments.

The Figures described above are a representative set, and are not an exhaustive with respect to embodying the invention.

DESCRIPTION

Disclosed are a system, method, and article of manufacture of embodiment training in a virtual-reality environment. The following description is presented to enable a person of ordinary skill in the art to make and use the various embodiments. Descriptions of specific devices, techniques, and applications are provided only as examples. Various modifications to the examples described herein can be readily apparent to those of ordinary skill in the art, and the general principles defined herein may be applied to other examples and applications without departing from the spirit and scope of the various embodiments.

Reference throughout this specification to "one embodiment," "an embodiment," 'one example,' or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

Furthermore, the described features, structures, or characteristics of the invention may be combined in any suitable manner in one or more embodiments. In the following description, numerous specific details are provided, such as examples of programming, software modules, user selections, network transactions, database queries, database structures, hardware modules, hardware circuits, hardware chips, etc., to provide a thorough understanding of embodiments of the invention. One skilled in the relevant art can recognize, however, that the invention may be practiced without one or more of the specific details, or with other methods, components, materials, and so forth. In other instances, well-known structures, materials, or operations are not shown or described in detail to avoid obscuring aspects of the invention.

The schematic flow chart diagrams included herein are generally set forth as logical flow chart diagrams. As such, the depicted order and labeled steps are indicative of one embodiment of the presented method. Other steps and methods may be conceived that are equivalent in function, logic, or effect to one or more steps, or portions thereof, of the illustrated method. Additionally, the format and symbols employed are provided to explain the logical steps of the method and are understood not to limit the scope of the method. Although various arrow types and line types may be employed in the flow chart diagrams, and they are understood not to limit the scope of the corresponding method. Indeed, some arrows or other connectors may be used to indicate only the logical flow of the method. For instance, an arrow may indicate a waiting or monitoring period of unspecified duration between enumerated steps of the depicted method. Additionally, the order in which a particular method occurs may or may not strictly adhere to the order of the corresponding steps shown.

Definitions

Biofeedback refers to a process of gaining greater awareness of many physiological functions primarily using instruments that provide information on the activity of those same systems, with a goal of being able to manipulate them at will. Some of the processes that can be controlled include brainwaves, muscle tone, skin conductance, heart rate and pain perception.

Gamification refers to the application of game-design elements and game principles in non-game contexts.

Machine learning can include the construction and study of systems that can learn from data. Example machine learning techniques that can be used herein include, inter alia: decision tree learning, association rule learning, artificial neural networks, inductive logic programming, support vector machines, clustering, Bayesian networks, reinforcement learning, representation learning, similarity and metric learning, and/or sparse dictionary learning.

Mobile device can include smart phones, cell phones, personal digital assistants, tablet computers, wearable computers, smart watches, smart glasses (e.g. Google Glass®), VR head-mounted displays (HMD), etc.

Virtual reality (VR) refers to a computer technology that uses VR headsets to generate realistic images, sounds and other sensations that simulate a user's physical presence in a virtual or imaginary environment. VR can utilize a combination of physical spaces or multi-projected environments as well. VR systems can include the transmission of vibrations and other sensations to the user through a haptic system(s).

Example Methods

FIG. 1 illustrates an example process for managing various therapeutic avatar animation exercises, according to some embodiments. In step 102, process 100 can provide a user avatar in a VR environment. The user avatar can represent all or various user body parts while the user is performing various therapeutic avatar animation exercises.

In step 104, process 100 can correlate the motions of the user avatar to the user's body. Therapeutic avatar animation exercises can be designed to induce the user to perform various body movements such as, inter alia: reach, grasp, wave, supination and pronation, left-right side bends, forward/backward flexion, left-right rotation, etc. These movements can have corresponding imagery with corresponding VR element body parts of the user avatar. The user avatar can be calibrated to the user's body through a calibration mechanism. The calibration mechanism can take into account user body size (e.g. height, weight, various specified proportions, arm span, shoulder span, male-female-gender neutral, joint alignment, limb length, etc.) in a clinical way to promote maximal clinical embodiment and feedback accuracy. In this way process 100 can determine a quality of user movement with respect to the therapeutic avatar animation exercises.

Various user-wearable and/or handheld position sensors can be used to track user motion. In one example, motion-tracked handheld controllers can be used to track user motion. User movements can be mapped to a virtual 3D space viewable via a virtual-reality head set. In this way, in step 106, process 100 can configure the user avatar to be controllable by a user. The user avatar can simultaneously perform a set of interactive and therapeutic avatar animations as the user. In step 108, a clinician can provide and then control a set of interactive and therapeutic avatar animation exercises to be performed by user via user avatar.

Process 100 can use room-scale tracking technology that allows the user to move in three-dimensional (3D) space. Process 100 can provide for the use of one or more motion-tracked handheld controllers for the user to interact with the virtual environment displayed to the user via the VR HMD. Process 100 can record user motions for later analysis by the clinician. User motions can be compared with idealized exercise motions such that quality of the user's motion can be determined. This information can be presented to the user and/or clinician via a mobile-device application dashboard, Web-based dashboard and the like. Process 100 can be gamified.

In one example, process 100 can randomize rewards in the style of biofeedback. In this way, a user can determine if the exercise was successfully performed. Feedback can auditory, visual, and/or haptic.

FIG. 2 illustrates an example process 200 of therapeutic avatar animation exercise manipulation, according to some embodiments. Process 200 can be integrated into process 100. In step 202, process 200 can identify a body part related to the therapeutic need of the user. In step 204, process 200 can generate a VR element representing the body part. In step 206, process 200 can incorporate a VR element into the user avatar. In step 208, process 200 can manipulate the angle of movement and/or the gain of the VR element with respect to actual physical movement of the body part.

For example, a user can be experiencing back pain. The user avatar can include a VR element representing the user's back (e.g. using body-part mirroring). The user can use process 100 to perform various back therapeutic avatar animation exercises. The movement of the VR element can be manipulated in the user's view of the VR environment. The angle of movement and the gain of the VR element related to actual physical movement of the user's back can be manipulated. For example, the angle of movement and gain for the VR element can be decreased or increased related to the user's actual physical movement to encourage the user to increase range of motion and/or other movement attributes. In one example, the user's view of the user avatar and or aspects of a therapeutic avatar animation exercise can be manipulated to encourage greater user exertion. For example, the user can be shown a decreased or increased view of the VR display in order to manipulate the user into completing an exercise.

A clinician can be provided a tool for adjusting the gain and/or other settings of a therapeutic avatar animation exercises. Returning to the lower-back mirroring, a user can 'hit' virtual ball targets leaning or bending. The clinician can modify how the user sees the virtual ball targets changing sensitivity and gain in order to motivate movement in the user. For example, if a person is experiencing too much reluctance to bend forward, the clinician can select to show the person a first-person VR view that bends less than his actual body in order to promote motivation. Alternately, if a person is extremely fearful of engaging at all, the clinician may begin the treatment by providing far more visual feedback than corresponds to physical movement in order to increase comfort with the concept of movement.

FIG. 3 illustrates an example process 300 for generating a diagnostic score for a user performing therapeutic avatar animation exercises, according to some embodiments. In step 302, process 300 can measure a set of user movement characters that correlate with a pain value experienced by the user doing a therapeutic avatar animation exercise. Characteristics correlated with pain can include, inter alia: pain free range of motion, angular velocity changes in 3D space, compensations, shakiness, jitter, etc. For example, more jitteriness can be an indicator of user compensation and guarding behavior with respect to pain. In one example, process 300 can receive and interpret user voice input to measure boundaries of user motion and/or pain values. For example, a user can say 'ouch' or other verbal indicators (e.g. grunting, 'this hurts', etc.) that a pain threshold has been reached. Process 300 can interpret these verbal indicators that the user is outside of the pain free range of motion. In one example, the pain free range of motion can be compared to a previous exercise or past date. It is noted that the quality of movement can be measured, in part, by an angular velocity of a positional sensor worn by the user. In one embodiment, angular velocity can be measured as follows:

$$\text{Sum of Angular velocity}/\#\text{ frames*coefficient=Functional Movement Score (FMS)}.$$

In step 304, process 300 can measure time of user reactions during the therapeutic avatar animation exercise. Time to react can correlate with pain, as well as, time to initiate a directed movement (e.g. can correlate to user fear/avoidance behavior). It is noted that models of the user's position (e.g. posture) through a directed movement can be generated.

In step 306, process 300 can generate a diagnostic score based on output of steps 302 and 304. Display the diagnostic score to a clinician to adjust therapeutic avatar animation settings. The diagnostic score can be looped back into the exercise system in order to tune the exercise system based on various patient's scores. Increases to a user's exposure in a systematic way can lead to progress.

The user can perform a progression of different exercises in which the movement of their first-person user virtual avatar is modified according to a parameter (e.g. amplification, gain change, gravity, mirroring, change in type of avatar). The user can perform each exercise in a progression that is grade (e.g. using process 300, etc.). The graded exposure can decondition the pain response from the movement of the affected body part, by moving in different contexts. In one example, in each exercise, the user can be prompted to move a body part in at least three (3) different ways with three (3) different activities, according to each parameter.

Figure 4:
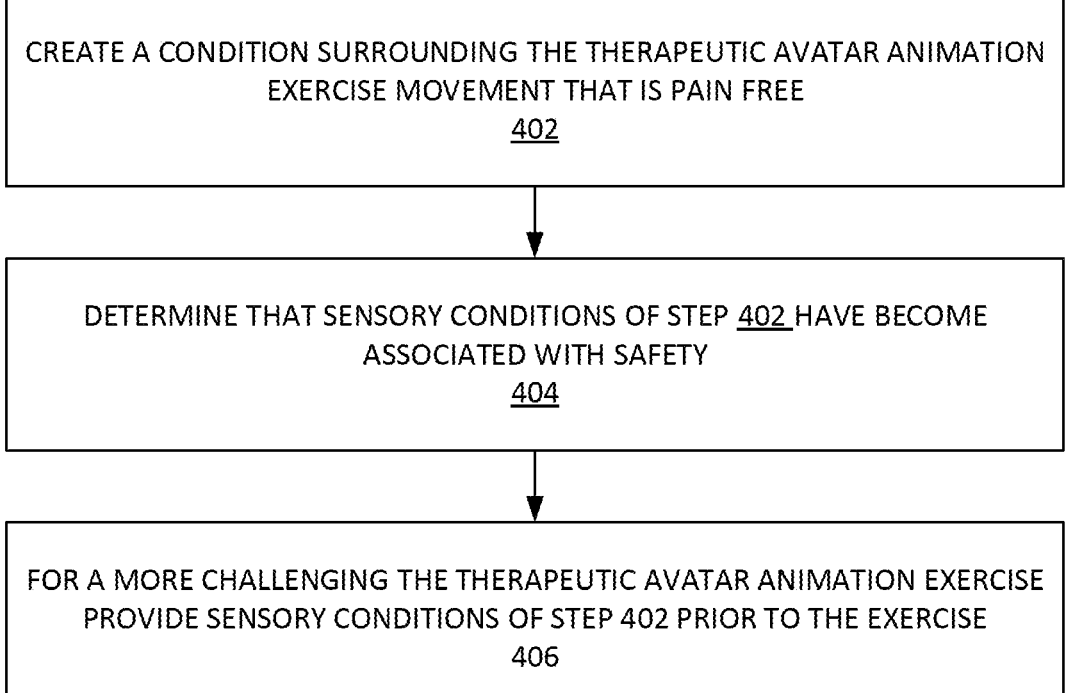
FIG. 4 illustrates an example process for deconditioning, according to some embodiments.

FIG. 4 illustrates an example process for deconditioning, according to some embodiments. In step 402, process 400 can create a condition surrounding the therapeutic avatar animation exercise movement that is pain free. The condition can include sound, sight, and haptic feedback. The patient immerses in this pleasant sensory environment to engage a feeling of safety and comfort. In step 404, process 400 can determine that sensory conditions of step 402 have become associated with safety. For example, once these sensory conditions have become associated with safety, they can be used to flood the patient before the patient is asked to initiate a more potentially painful movement in order to begin to draw an association between the previously considered painful movement, with the established safe sensory experience. It is used as an emotional safety anchor. In step 406, for a more challenging the therapeutic avatar animation exercise provide sensory conditions of step 402 prior to the exercise figure.

Example Systems and Architecture

As noted supra, various computer systems can be utilized by a system. For example, system can include a head-mounted display with a camera near the bottom rim; two wireless handheld controllers; and two 'lighthouse' base stations.

The system can include a virtual reality headset that is a head-mounted device that provides VR for the wearer. VR headsets are widely used can provide VR simulators and trainers. The VR headset can be a stereoscopic head-mounted display, stereo sound, and head motion tracking sensors. Head motion tracking sensors can include gyroscopes, accelerometers, structured light systems, etc. VR headsets can also include eye tracking sensors and gaming controllers in some example embodiments.

Figure 5:
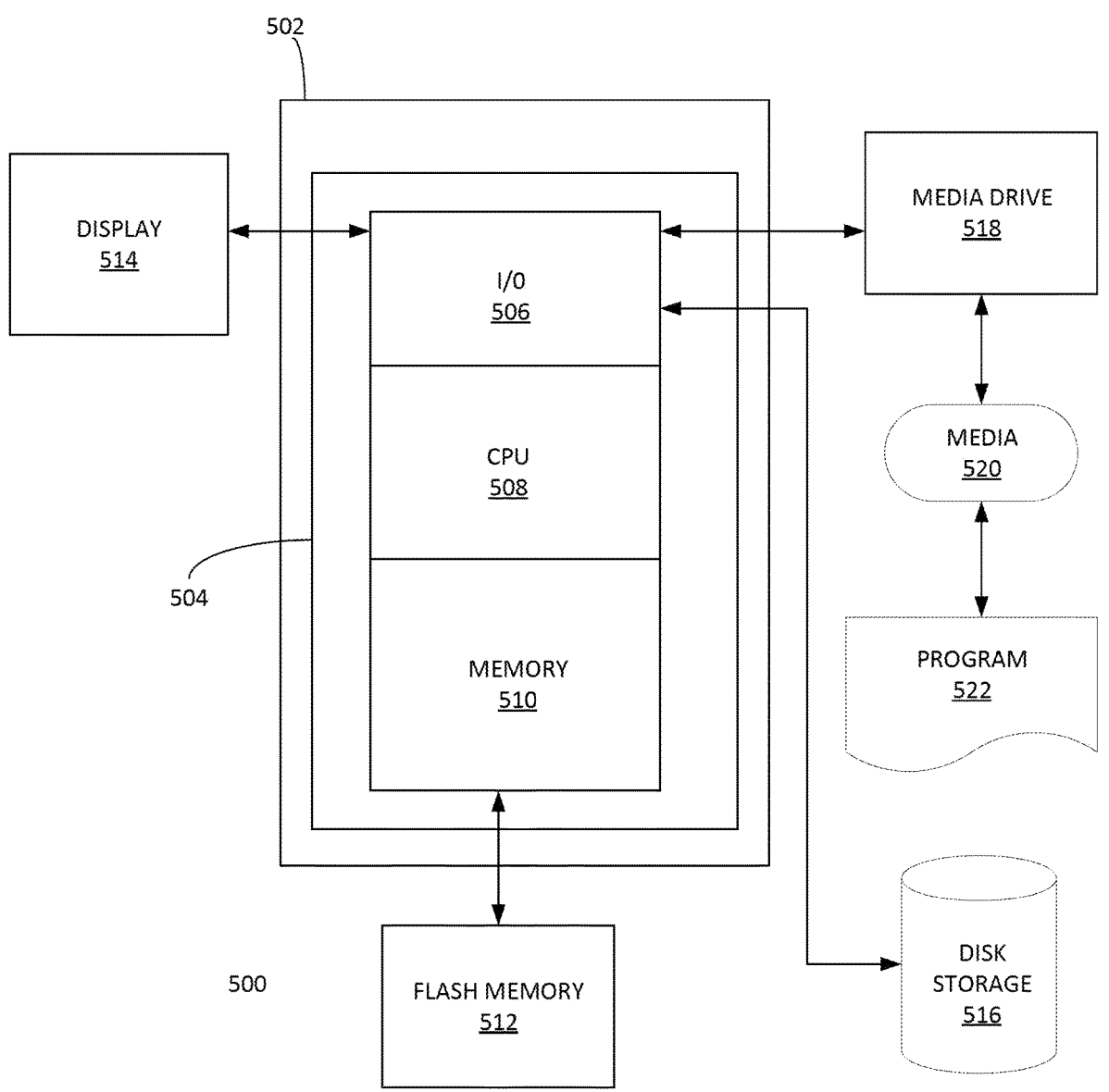
FIG. 5 depicts an exemplary computing system that can be configured to perform any one of the processes provided herein.

FIG. 5 depicts an exemplary computing system 500 that can be configured to perform any one of the processes provided herein. In this context, computing system 500 may include, for example, a processor, memory, storage, and I/O devices (e.g. monitor, keyboard, disk drive, Internet connection, etc.). However, computing system 500 may include circuitry or other specialized hardware for carrying out some or all aspects of the processes. In some operational settings, computing system 500 may be configured as a system that includes one or more units, each of which is configured to carry out some aspects of the processes either in software, hardware, or some combination thereof.

FIG. 5 depicts computing system 500 with a number of components that may be used to perform any of the processes described herein. The main system 502 includes a motherboard 504 having an I/O section 506, one or more central processing units (CPU) 508, and a memory section 510, which may have a flash memory card 512 related to it. The I/O section 506 can be connected to a display 514, a keyboard and/or other user input (not shown), a disk storage unit 516, and a media drive unit 518. The media drive unit 518 can read/write a computer-readable medium 520, which can contain programs 522 and/or data. Computing system 500 can include a web browser. Moreover, it is noted that computing system 500 can be configured to include additional systems in order to fulfill various functionalities. Computing system 500 can communicate with other computing devices based on various computer communication protocols such a Wi-Fi, Bluetooth® (and/or other standards for exchanging data over short distances includes those using short-wavelength radio transmissions), USB, Ethernet, cellular, an ultrasonic local area communication protocol, etc.

Figure 6:
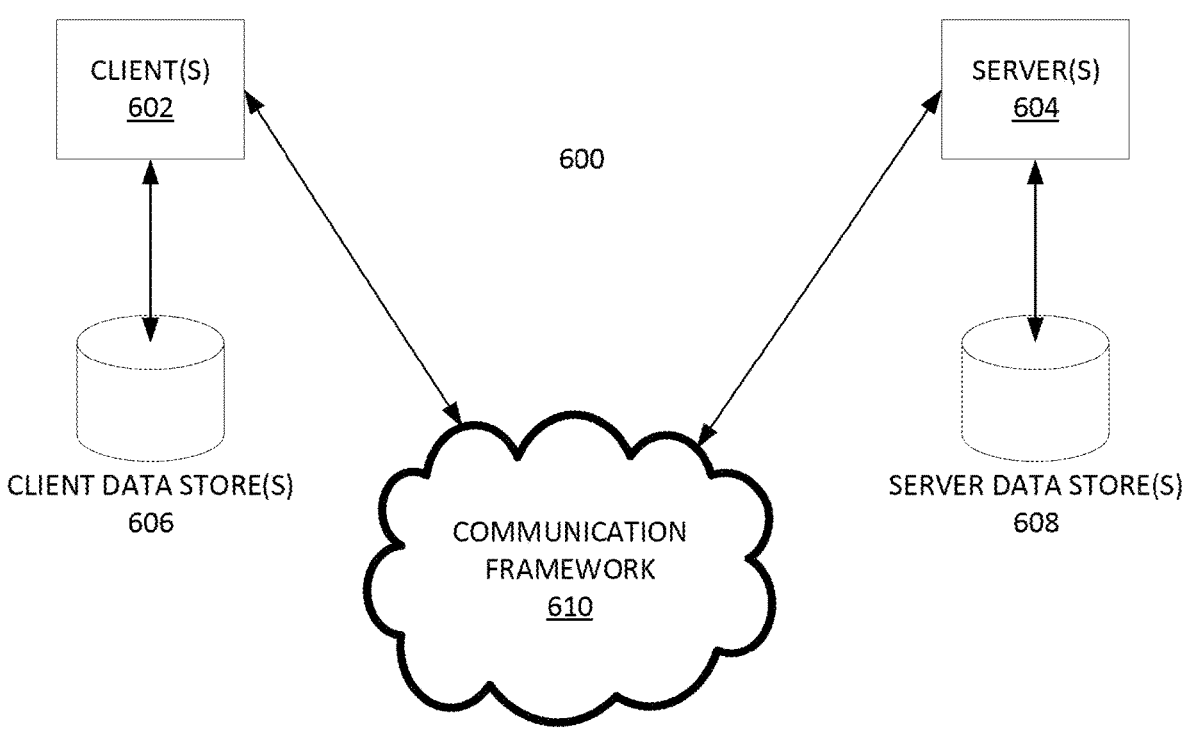
FIG. 6 is a block diagram of a sample computing environment that can be utilized to implement various embodiments.

FIG. 6 is a block diagram of a sample computing environment 600 that can be utilized to implement various embodiments. The system 600 further illustrates a system that includes one or more client(s) 602. The client(s) 602 can be hardware and/or software (e.g., threads, processes, computing devices). The system 600 also includes one or more server(s) 604. The server(s) 604 can also be hardware and/or software (e.g., threads, processes, computing devices). One possible communication between a client 602 and a server 604 may be in the form of a data packet adapted to be transmitted between two or more computer processes. The system 600 includes a communication framework 610 that can be employed to facilitate communications between the client(s) 602 and the server(s) 604. The client(s) 602 are connected to one or more client data store(s) 606 that can be employed to store information local to the client(s) 602. Similarly, the server(s) 604 are connected to one or more server data store(s) 608 that can be employed to store information local to the server(s) 604. In some embodiments, system 600 can instead be a collection of remote computing services constituting a cloud-computing platform. Alternatively, in some examples, system 600 can be implement in a cloud-computing environment.

Additional Embodiments

Figure 7:
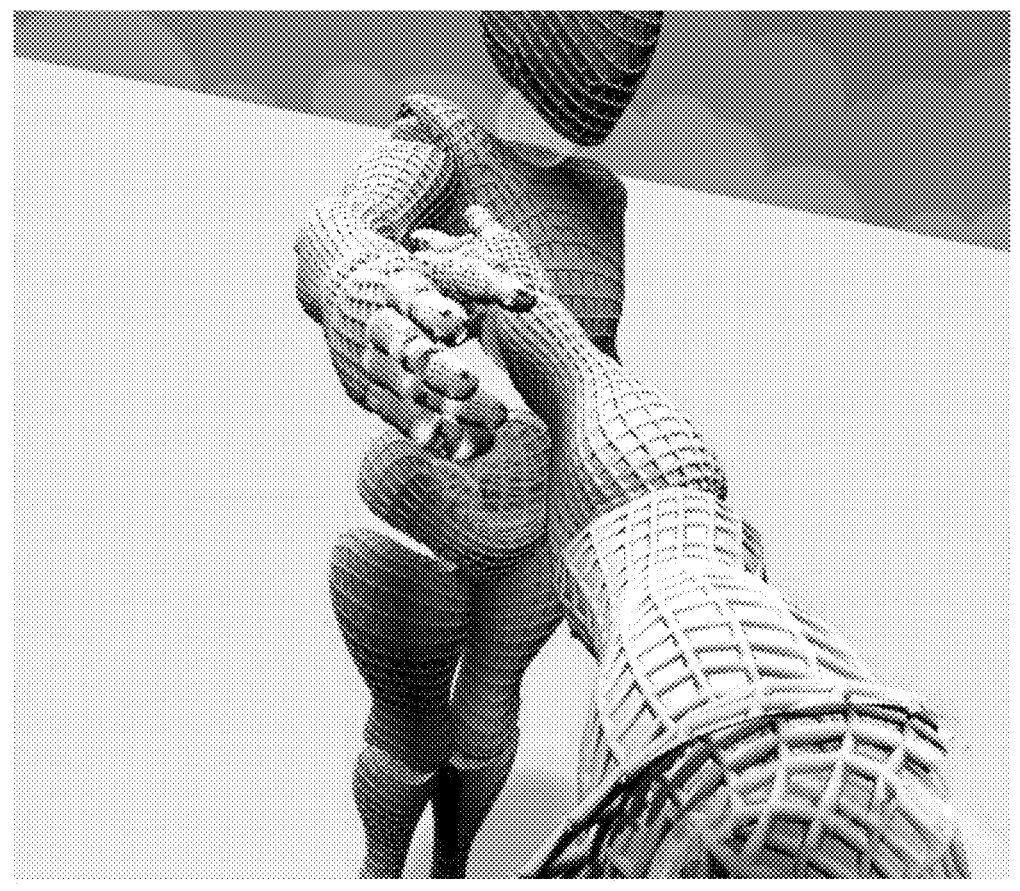
FIG. 7 illustrates a first-person view of embodied virtual reality, according to some embodiments.

FIG. 7 illustrates a first-person view 700 of embodied virtual reality, according to some embodiments. View 700 illustrates how a subject views a first-person arm reaching to shake the arm of another avatar. In reality, the subject is not moving his or her own limbs. View 700 is an example of an exercise is taken from a motor imagery module for upper limb exercises.

Figure 8:
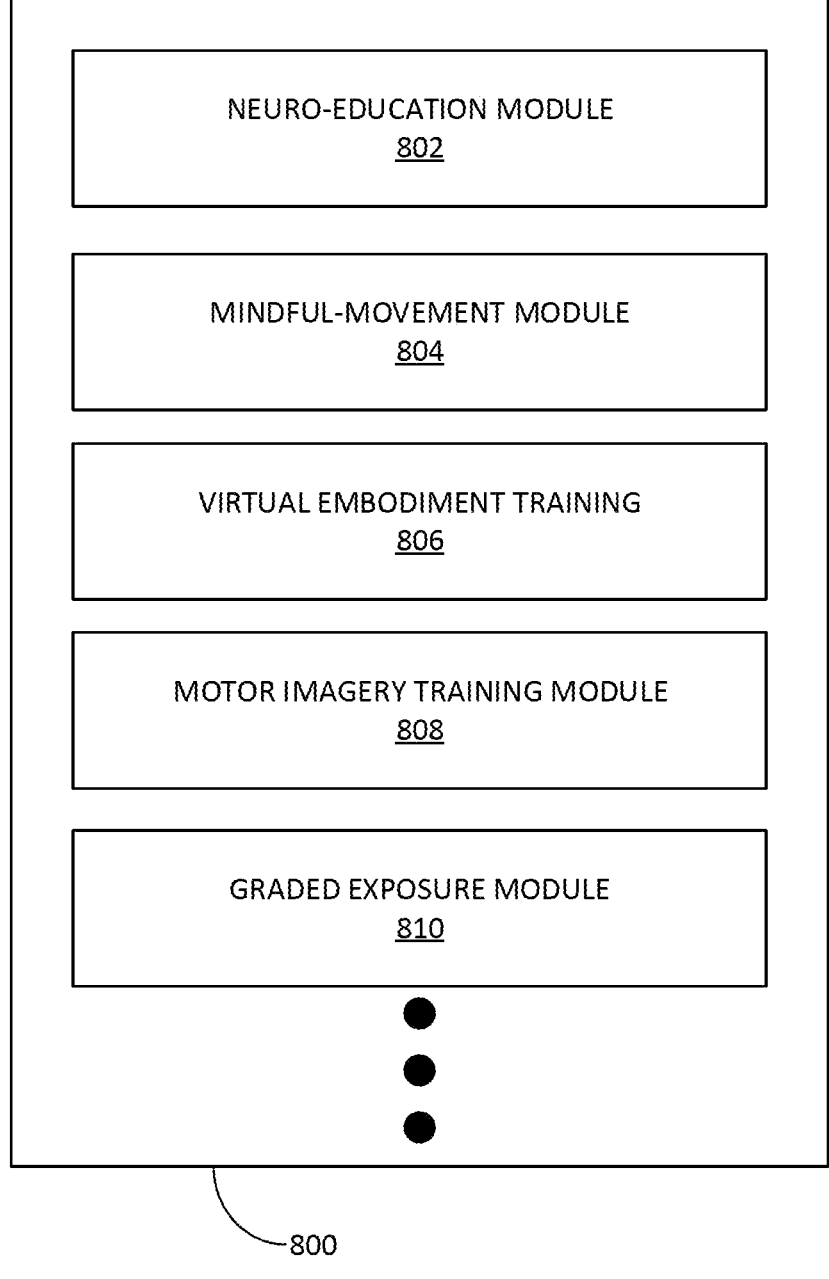
FIG. 8 illustrates an example VR embodiment training system, according to some embodiments.

FIG. 8 illustrates an example VR embodiment training system 800, according to some embodiments. VR embodiment training system 800 can be used to implement the various methods provided herein. VR embodiment training system 800 can include a neuro-education module 802. Neuro-education module 802 can manage the presentation of various VR education sessions. A VR education sessions can explain the concepts behind the VR exercise. A VR education session can provide a video/audio content that describes a neurological/therapy concept to a user in an immersive VR environment. For example, the VR education session can provide a VR tour of the human nervous system. This VR tour can start at the outline of the nervous system beginning with the human brain, travel down the spine, then move out to the peripheral portions of the human nervous system. The VR tour can include audio media of a clinician explaining the portion of the human nervous system in the user's VR view. The audio media can explain how the user's nervous system becomes sensitized. The VR education session can include with a specified VR exercise for the user. The VR exercise can be related to the topic of the VR education session. Accordingly, the user can then be guided through the VR exercise. Neuro-education module 802 can store and obtain a set of VR education sessions (e.g. a neuro-education curriculum) in a database. Neuro-education module 802 can provide a means (e.g. a dashboard, mobile application interface, etc.) for a therapist to select a respective VR education session for a patient. The therapist can also monitor the patient/user's progress through one or more assigned VR education sessions.

VR embodiment training system 800 can include Mindful-Movement module 804. Mindful-Movement module 804 can present a VR-version of a generic human body as the body of the user. Mindful-Movement module 804 can provide a guided tour of the generic human body. Mindful-Movement module 804 can access a database of Feldenkrais Method exercise therapies and concomitant VR video/audio descriptions. These exercise therapies can be used to reorganize connections between the brain and body and thus improve user/patient body movement and psychological state. Mindful-Movement module 804 can access biofeedback sensor data from the user. Based on user jitter (and/or other user body-movement sensor data) the Mindful-Movement module 804 can modify the color and/or other attributes of the VR scene experienced by the user. The therapist can toggle and modify various parameters of this mindful movement experience. Mindful-Movement module 804 can provide various biofeedback experiences to the user along with guided audio content. Mindful-Movement module 804 can manage an induction step where the user moves in certain ways to induce the movement of the user's virtual avatar. Mindful-Movement module 804 can synchronize the user's motion and the virtual avatar's motion. The user's movements can be guided by the VR video/audio descriptions of a Feldenkrais practitioner. The user can see the users' virtual avatar performing the Feldenkrais exercises that mirror the user's own movements. This can be a means for inducing embodiment of a user's virtual avatar.

VR embodiment training system 800 can include Virtual Embodiment Training (VET) module 806. VET module 806 can display the user's VR body in positions and/or motions that the user may not be able to produce in his/her real-world body. These positions and/or motions can be provided as the user performs various VR therapy exercises. For example, VET module 806 can provide laterality training exercise in a VR environment. The user can be provided various images of a right arm or a left arm for the user to identify. If the user's success rate passes a specified parameter, the user can move on to other exercises such as motor-imagery training. In this way, the user can learn laterality.

VR embodiment training system 800 can include Motor Imagery Training module 808. Motor Imagery Training module 808 can provide a set of VR therapy exercises in which a user simulates various movements. The user can select a set of VR therapy exercises for a portion of the user's body. For example, the user can select upper-body limbs. The first exercise can be handshake simulations in a VR environment (e.g. see FIG. 7). The user can also reach for various VR objects for a specified number of repetitions. Motor Imagery Training module 808 can also provide mirroring exercises, trunk rotation exercises, etc.

VR embodiment training system 800 can include Graded Exposure module 810. Graded Exposure module 810 can provide the user a set of VR therapy exercises designed to expose the user to an increasing motion gradient. These VR therapy exercises can be used as a test for the user. In this way, a user's current state can be determined. More and more difficult VR therapy exercises can be provided to the user as the user improves. These VR therapy exercises can include analogue world experiences such as, a set of kitchen motions, stocking goods motions, other occupation movements, etc. The graded exposure VR therapy exercises can be tuned based on a smoothness of the user's movement. For example, is a user can perform a movement in a smooth manner (e.g. low jitter sensed by jitter sensors worn by the user), then the user's VR targets can be placed at a great distance for the user. In this way, the user's rotation motions, reach motions, and the like can be increased for greater therapeutic benefit. For example, fifteen degrees of rotation can be expanded to seventeen degrees of motion and then eighteen degrees of motion until the user eventually reaches a maximum range of motion.

It is noted that VR embodiment training system 800 can provide web-portal non-VR based versions of the VR exercises and content as well.

FIG. 9 illustrates an example process 900 for augmenting VR-based therapeutic movements, according to some embodiments. Process 900 can provide various therapeutic VR exercises and gameplay elements. The therapeutic VR exercises ROM and gameplay elements are ergonomically placed for individual user's therapeutic exercise abilities. Process 900 can tune target ROM and display a VR avatar with a higher ROM to induce increased ROM in the user.

For example, process 900 can use ergonomic calculations to determine where to place bubbles in a VR-based therapeutic bubble touching game. The location of the bubbles can be located to augment the angular adjustment of the user's ROM during the therapeutic exercise by 10-20%. Process 900 can be performed in with a home-based VR system (exercise(s) can be automatically loaded and provided in an optimal sequence, etc.) and/or at a physical therapy office (exercise(s) can be loaded by physical therapist, physician or other medical professional).

More specifically, in step 902, process 900 can obtain user information relevant to therapeutic exercise. In step 904, process 900 can factor output of step 902 against national model(s) for what rom should be. In step 906, process 900 can provide a VR view of an avatar performing therapeutic exercise based on output of 908. In step 908, process 900 can user performs therapeutic exercises and track user performance thereof. In step 910, process 900 can generate a VR view of an avatar performing of the user performing therapeutic exercise based on output of 908. In step 912, process 900 can adjust VR view of user's avatar at specified portions of the therapeutic exercise to simulate and/or approximate national models.

Process 900 can estimate muscle tension based on physical simulation of body part(s) involved in the therapeutic exercise. Process 900 can use rigid body stimulation to estimate muscle tensions. Process 900 can implement augmentations and dampening of the therapeutic exercise. This can be done on the basis space of the muscle tension not just in angle. Process 900 and graph the movement of the ROM of each repetition. Process 900 can graph out wobbliness at different points of the therapeutic exercise as well. Process

900 can graph and model wobbliness use this information to implement ROM augmentation. Process 900 can graph tremors at points along the ROM. Tremors/wobbliness can be related to different muscle fibers.

As noted, process 900 can implement ergonomic placement of virtual gameplay elements. Augmentation with dynamics can be implemented. Process 900 can normalize therapeutic exercise ROM by weight of limb(s) involved. The therapeutic exercise can be tuned for different people. Process 900 can utilize ergonomic definitions for range of motion augmentation. Process 900 can provide a sequence of augmentation for pain therapy purposes (e.g. educate, measure, explore, augment, underplay, cooldown, etc.). Process 900 can utilize VR to visualization of range of motion. Process 900 can be used for ergonomic gameplay based on range and therapeutic purposes. Process 900 can provide specific activities of daily living as therapy practices, etc. Process 900 can provide the visualization of pain in specific manners in a VR environment. Process 900 can provide VR-based visualizations for acceptance-commitment-therapy, etc.

FIG. 10 illustrates an example process 1000 for correlating features of a user's motion in a VR-based exercise/motion with specified populations, according to some embodiments. In step 1002, process 1000 can use datapoints obtained from position of hand controller (e.g. see FIG. 11). In step 1004, process 1000 can extract a dynamic range (e.g. how far the user reached in the x, y and z plane, etc.). In step 1006, process 1000 can, from data obtained/determined in steps 1002 and 1004, determine a velocity, acceleration, variability in velocity and acceleration. In step 1008, process 1000 can determine the coefficient of variation for the extracted features. In step 1010, process 1000 can, from the acceleration and velocity data, calculate the initiation of movement. In step 1012, process 1000 can measure variables such as, inter alia: dynamic range and variability within initiation. In step 1014, process 1000 can use a combinatorial statistic to determine which features correlate to specified populations. Example populations can include, inter alia: healthy populations, populations with specified disease states, populations with specified muscular skeletal injuries/degenerations, populations with shoulder pain, populations with upper extremity chronic pain, etc.).

Figure 11:
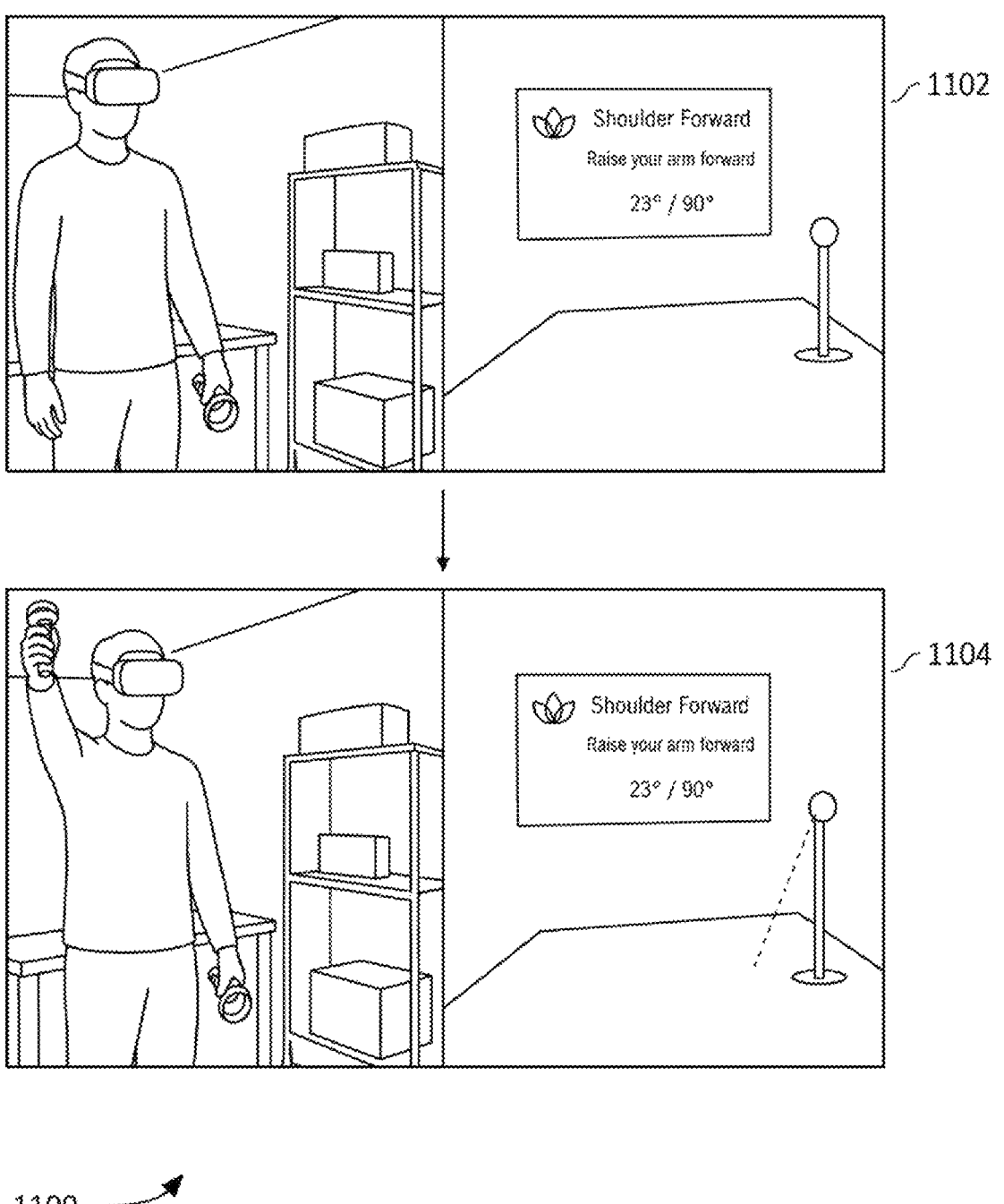
FIG. 11 illustrates an example process of measuring a specified ROM of a user therapeutic motion, according to some embodiments.

FIG. 11 illustrates an example process 1100 of measuring a specified ROM of a user therapeutic motion, according to some embodiments. The user can wear hand controllers and VR headset. Step 1102 shows the user in a beginning position. Step 1104 shows the user in an arms raised to a specified degrees of ROM (e.g. hundred and eighty-degree (180°) ROM, etc.). The data from the hand controllers and VR headset can be used to track user motion. Process 1100 can then calculate shoulder angle as the estimation between relative points between head and hand controller.

Figure 12A:
FIGS. 12 A-C illustrate additional information obtained from processes 1000 and 1100, according to some embodiments.
Figure 12B:
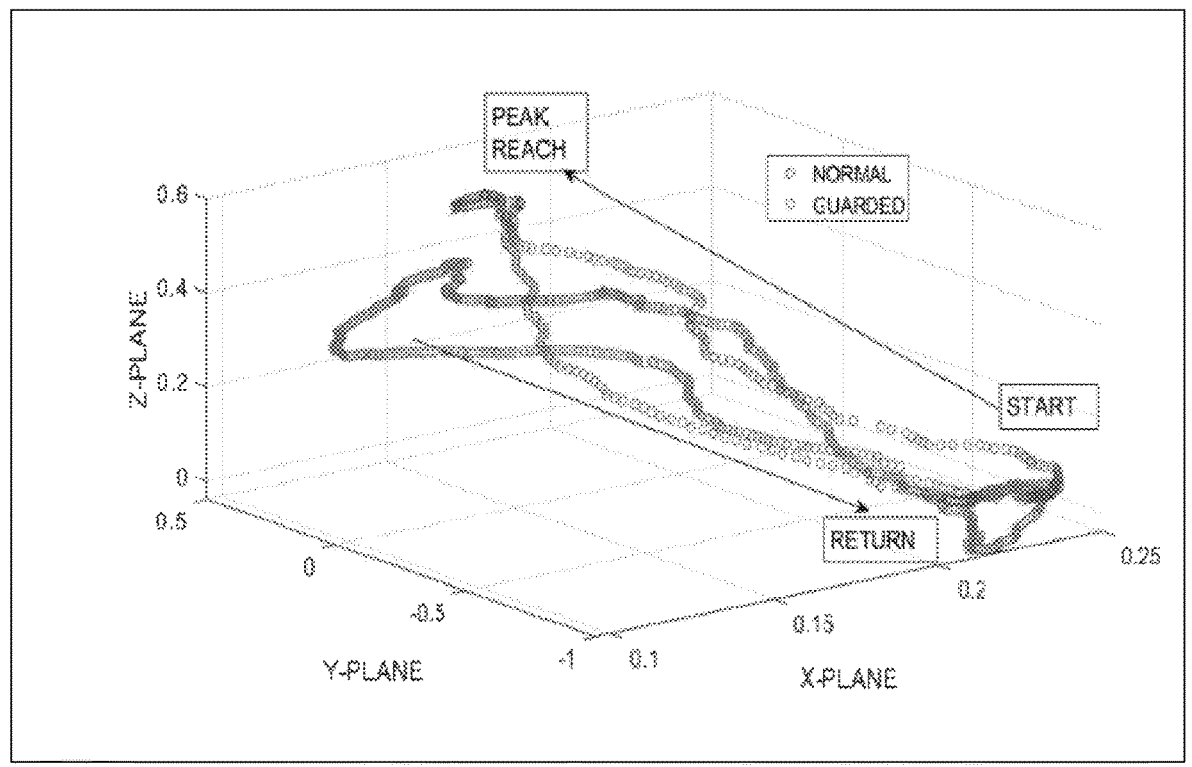
Figure 12C:
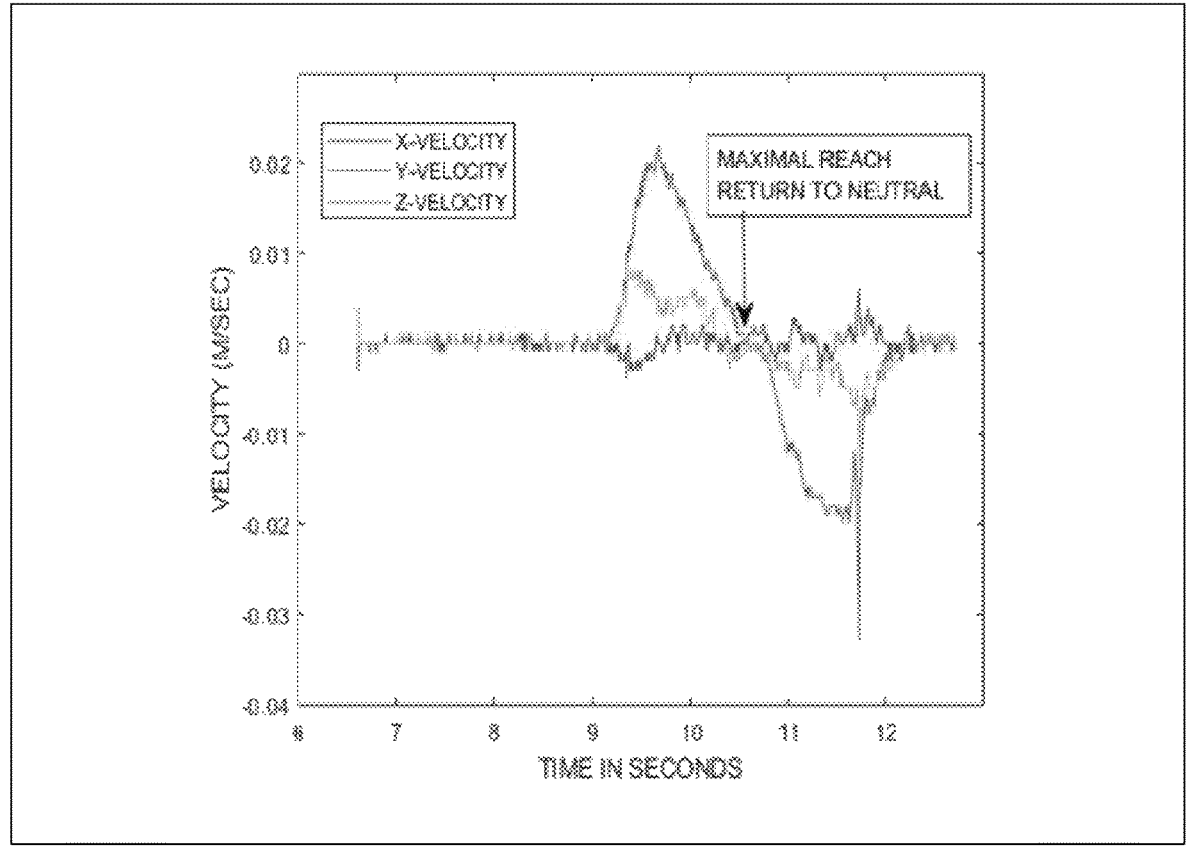

FIGS. 12 A-C illustrate additional information obtained from processes 1000 and 1100, according to some embodiments. This data can be used to correlate features of a user's motion in a VR-based exercise/motion with specified populations. More specifically, FIG. 12A illustrates an example data set of extracted features 1202, according to some embodiments. Extracted features 1202 can be obtained from user's motion in a VR-based exercise/motions.

FIG. 13 illustrates an example process 1300 for utilizing extracted features obtained on the three dimensions of VR-based exercise/motion for an example user motion for diagnosis of health/injury/impairment, according to some embodiments. As shown, in step 1302, a set of extracted features can be obtained for a healthy 'normal' population.

The extracted features can be obtained on three dimensions of VR-based exercise/motion. The dynamic range of the set of healthy users' VR-based exercise/motion can be obtained for each dimension. Various statistical parameters can be obtained with respect to the dynamic range of the set of healthy users' VR-based exercise/motion in three dimensions. For example, as shown, a coefficient of variation can be obtained for each dimension.

In step 1304, other sets of extracted features can be obtained for injured/impaired populations. Again, the extracted features can be obtained on the three dimensions of VR-based exercise/motion. The dynamic range of the set of injured/impaired users' VR-based exercise/motion can be obtained for each dimension. Various statistical parameters can be obtained with respect to the dynamic range of the set of injured/impaired users' VR-based exercise/motions in three dimensions. For example, as shown, a coefficient of variation can be obtained for each dimension.

In step 1306, the extracted features of a particular user can also be obtained. The extracted features can be obtained on the three dimensions of VR-based exercise/motion.

In step 1308, the user's extracted features can then be compared with the statistical parameters of the set of injured/impaired users' VR-based exercise/motions in three dimensions and the healthy users' VR-based exercise/motions in three dimensions. In this way, in step 1310, the user's health/injury/impairment state can be determined. It is noted that the extracted features can be obtained on the three dimensions of VR-based exercise/motion for a plurality of VR-based exercise/motions. These can include a VR-based exercise/motions of various sets of muscles, limbs, etc. The user can perform the same VR-based exercise/motions and the extracted features of the user can be compared against multiple sets of healthy/impaired extracted feature data. In some examples, process 1000 can be used to implement process 1300.

Returning to FIGS. 12 A-C, FIGS. 12 B-C illustrate example graphs of extracted features obtained on the three dimensions of VR-based exercise/motion for an example user VR-based exercise/motion. As shown, the extracted features obtained on the three dimensions of VR-based exercise/motion in various ways to enable further analysis and thus diagnosis of user health/injury/impairment states. In one example, a computerized method for extracting and interpreting features of a user's motion in a VR-based exercise with specified populations includes the step of tracking a user's motion in a VR-based exercise with head mounted display two hand controllers. Based on a set of datapoints obtained from a sequence of positions of two hand controllers the method extracts motion characteristics of the user's motion. Based on motion characteristics, the method determines velocity, acceleration, dynamic range, and variability of the user's motion. The method determines the coefficient of variation for the velocity and the acceleration. From the acceleration and velocity data, the method calculates multivariate characteristic of motion. The method further classifies motion based on a combinatorial statistic from extracted features. The method determines a set of features of the user's motion represented by the combinatorial statistic that correlates to another combinatorial statistic associated with a specified population. It is noted that sample population data can be used for feature extraction and/or combinatorial statistics (e.g. using clustering analysis such as inter alia: connectivity models, centroid models, distribution models, density models, group models, neural models, hierarchal clustering overlapping clustering, subspace models, etc.).

CONCLUSION

Although the present embodiments have been described with reference to specific example embodiments, various modifications and changes can be made to these embodiments without departing from the broader spirit and scope of the various embodiments. For example, the various devices, modules, etc. described herein can be enabled and operated using hardware circuitry, firmware, software or any combination of hardware, firmware, and software (e.g. embodied in a machine-readable medium). In addition, it can be appreciated that the various operations, processes, and methods disclosed herein can be embodied in a machine-readable medium and/or a machine accessible medium compatible with a data processing system (e.g. a computer system) and can be performed in any order (e.g. including using means for achieving the various operations). Accordingly, the specification and drawings are to be regarded in an illustrative rather than a restrictive sense. In some embodiments, the machine-readable medium can be a non-transitory form of machine-readable medium.

What is claimed is:

1. A computerized method for extracting and interpreting features of a user's motion in a virtual reality (VR)-based exercise with specified populations comprising:

tracking a user's motion in a VR-based exercise with a head mounted display, a set of jitter sensors worn by a user, and two hand controllers;

based on a set of datapoints obtained from a sequence of positions of the two hand controllers, extracting a set of motion characteristics of the user's motion;

based on motion characteristics, determining a velocity, an acceleration, a dynamic range, and a variability of the user's motion;

determining a coefficient of variation for the velocity and the acceleration;

based on the dynamic range, determining a variability in velocity and a variability of acceleration of the user's motion;

determining the coefficient of variation for the variability in velocity and the variability of acceleration of the user's motion;

from the acceleration and velocity data, calculating a multivariate characteristic of motion;

classifying a motion based on a combinatorial statistic from the extracted features;

determining a set of features of the user's motion represented by the combinatorial statistic that correlates to another combinatorial statistic associated with a specified population;

displaying a VR view of an avatar of the user performing the VR-based exercise, wherein the avatar of the user performs the VR-based exercise at a greater range of motion than the user, wherein the specified population comprises a population with a specified muscular skeletal injury, comparing the set of features of the user's motion with a set of statistical parameters of the set of injured users' VR-based motions, and determining, based on the comparing, a health, injury, or impairment state of the user;

obtaining a user range of motion (ROM) relevant to a VR-based therapeutic exercise;

comparing the user ROM against an aspirational model ROM for the VR-based therapeutic exercise; and

adjusting a VR view of an avatar of the user at one or specified portions of the VR-based therapeutic exercise to simulate the aspirational model ROM;

with a set of jitter sensors worn by the user, measuring a jitter of the user performing the VR-based exercise; and, when a user performs a movement in a smooth manner as indicated by low jitter sensed by the jitter sensors worn by the user, placing VR targets at a greater distance for the user and expanding a degree of motion from a first degree to a second degree;

as the jitter of the user performing the VR-based exercise decreases, increasing the range of motion of the VR-based exercise;

receiving and interpreting a user voice word input to measure a boundary of user motion with respect to a pain threshold, and wherein the voice word input comprises a plurality of verbal word indicators that the user is outside of a pain free range of motion;

measuring a set of user movement characteristics that correlate with a pain value experienced by the user doing a therapeutic avatar animation exercise, wherein the set of user movement characteristics comprises pain free range of motion, angular velocity changes in 3D space, compensations, shakiness, or jitter;

comparing the set of features of the user's motion with an idealized exercise motion and determining a quality of the user's motion, wherein the quality of movement is measured by an angular velocity of a positional sensor worn by the user; and generating a diagnostic score based on output of (i) the measuring of the set of user movement characteristics and (ii) measuring time of user reactions during the therapeutic avatar animation exercise, and displaying the diagnostic score to a clinician to adjust therapeutic avatar animation settings.

2. The computerized method of claim 1, wherein the dynamic range comprising a reach distance of the user reached in an x-plane, a y-plane and a z-plane.

3. The computerized method of claim 2, wherein the specified population comprises a healthy populations, a population with specified disease state, a population with a specified muscular skeletal injury, a population with shoulder pain or a population with an upper extremity chronic pain.

4. The computerized method of claim 1 further comprising:

measuring the dynamic range and variability within initiation of the user's motion.

* * * * *